(12) United States Patent
Dam-Huisman et al.

(10) Patent No.: US 11,553,980 B2
(45) Date of Patent: Jan. 17, 2023

(54) SYSTEM AND METHOD FOR DIRECTING A CONDUIT WITHIN A SURGICAL FIELD

(71) Applicant: Crea IP B.V., Vierpolders (NL)

(72) Inventors: Adriaantje Coliene Dam-Huisman, Delfgauw (NL); Claus Eckardt, Bad Homburg (DE)

(73) Assignee: Crea IP B.V., Vierpolders (NL)

( * ) Notice: Subject to any disclaimer, the term of this patent is extended or adjusted under 35 U.S.C. 154(b) by 350 days.

(21) Appl. No.: 16/761,820

(22) PCT Filed: Oct. 23, 2018

(86) PCT No.: PCT/NL2018/050698
§ 371 (c)(1),
(2) Date: May 6, 2020

(87) PCT Pub. No.: WO2019/093879
PCT Pub. Date: May 16, 2019

(65) Prior Publication Data
US 2021/0186646 A1     Jun. 24, 2021

(30) Foreign Application Priority Data
Nov. 8, 2017   (NL) ..................................... 2019868

(51) Int. Cl.
*A61F 9/007*     (2006.01)
*A61B 90/35*     (2016.01)
*A61B 90/30*     (2016.01)

(52) U.S. Cl.
CPC .............. *A61B 90/35* (2016.02); *A61F 9/007* (2013.01); *A61B 2090/306* (2016.02); *A61B 2217/005* (2013.01); *A61B 2217/007* (2013.01)

(58) Field of Classification Search
CPC . A61B 90/35; A61B 2090/306; A61B 3/0008; A61F 9/007; A61F 9/00736
USPC ......................................................... 600/249
See application file for complete search history.

(56) References Cited

U.S. PATENT DOCUMENTS

| 5,217,465 A * | 6/1993 | Steppe ................... A61M 1/84 606/1 |
| 5,681,264 A * | 10/1997 | Ryan, Jr. ................ A61F 9/007 606/4 |
| 2016/0051335 A1 * | 2/2016 | Richmond ............. A61B 90/36 600/249 |

FOREIGN PATENT DOCUMENTS

WO              93/16668 A1      9/1993

* cited by examiner

*Primary Examiner* — Si Ming Ku
(74) *Attorney, Agent, or Firm* — N.V. Nederlandsch Octrooibureau

(57) ABSTRACT

A system for positioning a conduit within an ophthalmic surgical field comprises a conduit (12), a first fixation point (14) and a second fixation point (15). The first fixation point (14) comprises base structure (16) arranged to be secured in a fixed location, and a grip arrangement (18) configured to hold the conduit (12). The grip arrangement (18) is mounted on the base structure (16) by way of a ball joint structure (20, 22), with the ball joint structure (20, 22) being arranged to allow pivoting and rotational movement of the grip arrangement (18) with respect to the base structure (16). The second fixation point (15) is positioned remote from the first fixation point (14) at a predefined distance therefrom. A method for positioning a conduit with an ophthalmic surgical field is also described.

21 Claims, 4 Drawing Sheets

Figure 1:
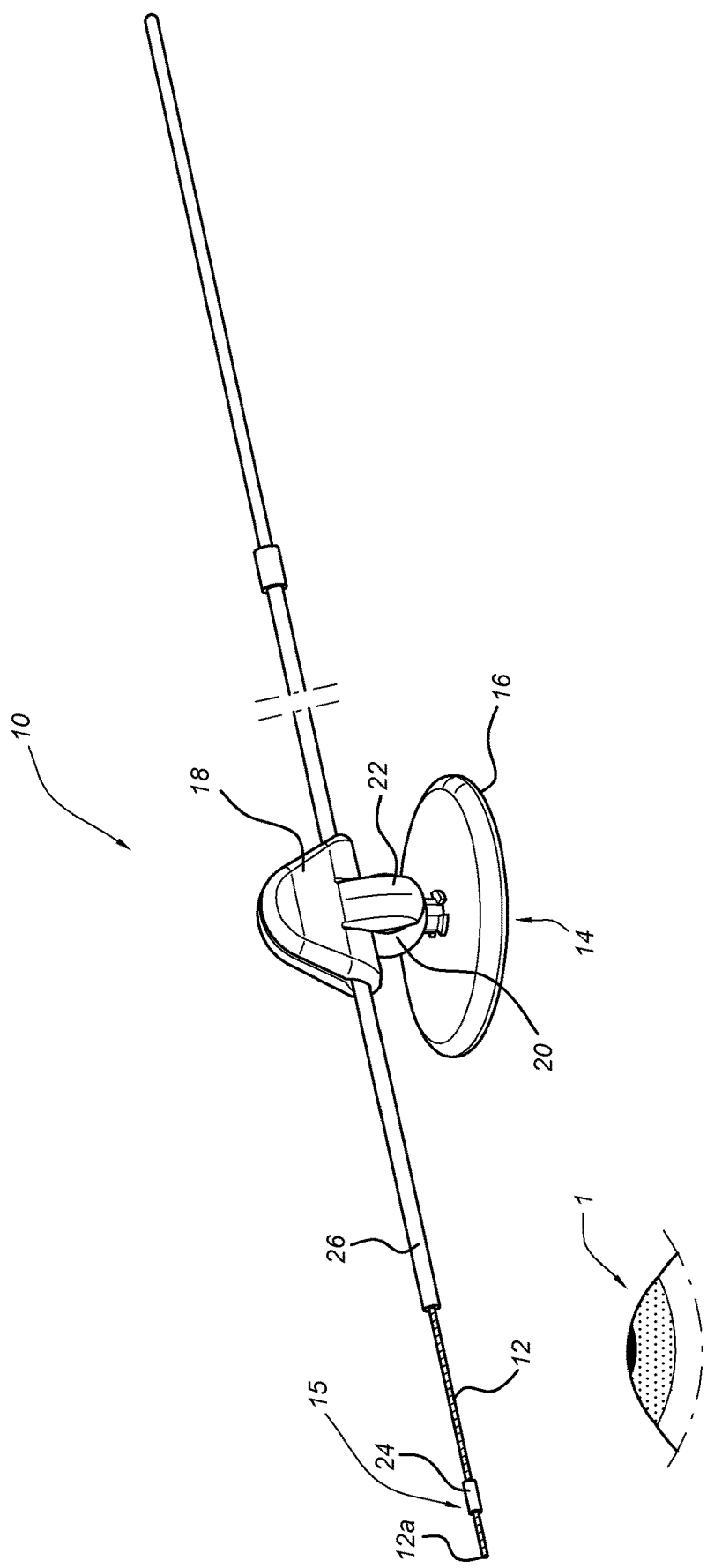

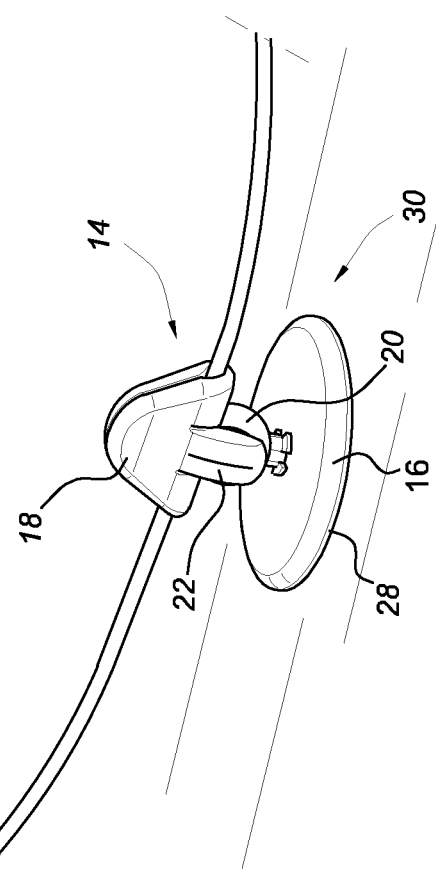
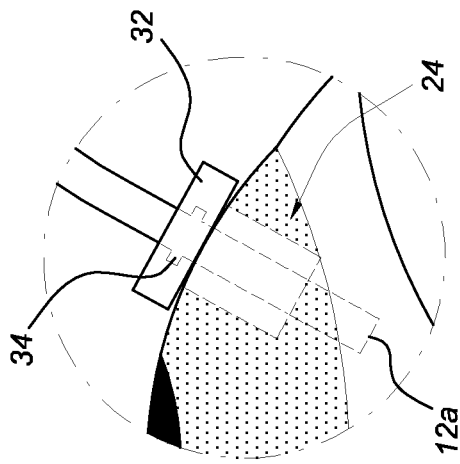
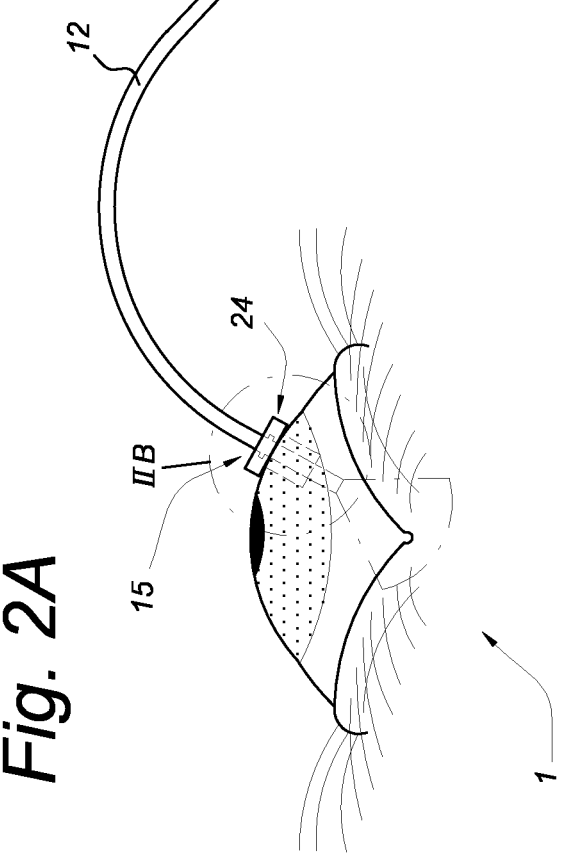

SYSTEM AND METHOD FOR DIRECTING A CONDUIT WITHIN A SURGICAL FIELD

FIELD OF THE INVENTION

The present invention relates to a system and method for directing a conduit within a surgical field, and more particularly to a system and method for steering the tip of an optical fibre or a fluid conduit within the eye.

BACKGROUND ART

Systems for use in ophthalmic surgery often comprise conduits for delivering light or fluids into the eye. For example, an apparatus for illuminating the surgical field may comprise a lumen through which an optical fibre coupled to a light source extends. In addition to light for illuminating the surgeon's field of view, optical fibres may also deliver radiation for treatment to a site within the eye. In some applications, fluid transport lumens may also be provided, which deliver fluid (e.g. irrigation and/or aspiration fluid) to the eye. For example, the fluid conduit may be connected to a fluid source (e.g. an infusion bottle) and configured to deliver irrigation fluid to the surgical site. Alternatively, the fluid conduit may be connected to a vacuum source and configured to aspirate fluid and surgical debris from the eye. In many applications, it may be useful to be able to steer the tip of the conduit within the eye to direct illumination and/or fluid flow to a precise location within the eye.

U.S. Pat. No. 5,681,264 A describes an illumination device for ophthalmic surgery. The device comprises an optical fibre with a proximal end and a distal end, a connector disposed at the proximal end of the optical fibre and a hand-piece disposed generally at the distal end of the optical fibre. To orient the illumination to the desire location within the eye, the user manipulates the hand-piece to move the field of illumination within the eye.

PCT Publication No. WO 93/16668 A1 describes a flexible and steerable aspiration tip for use during microsurgery. The aspiration tip includes a flexible portion which includes a spring material therewith which may be configured in a relaxed and pre-curved state or, alternatively, a stressed and straight configuration. The aspiration tip may be combined with a hand-piece assembly which includes means to remotely alter the configuration of the aspiration tip.

SUMMARY OF THE INVENTION

The present invention seeks to provide an improved system and method for orienting the tip of a conduit within a surgical field during ophthalmic surgery.

According to the present invention, there is provided a system for positioning a conduit within an ophthalmic surgical site or surgical field, the system comprising: a conduit; a first fixation point comprising a base structure arranged to be secured in a fixed location, and a grip arrangement configured to hold the conduit, the grip arrangement being mounted on the base structure by way of a ball joint structure, the ball joint structure being arranged to allow pivoting and rotational movement of the grip arrangement with respect to the base structure, and a second fixation point positioned remote from the first fixation point at a predefined distance therefrom.

According to a second aspect of the invention, there is provided a method for positioning a conduit within a surgical site or surgical field, the method comprising: securing a conduit at a first fixation point, the first fixation point comprising a base structure configured to be secured to a surface and a grip arrangement configured to hold the conduit, the grip arrangement being mounted on the base structure by way of a ball joint structure arranged to allow pivoting and rotational movement of the grip arrangement with respect to the base structure; securing the conduit at a second fixation point at an entry point of the surgical field, wherein the second fixation point is positioned remote from the first fixation point and a predetermined distance therefrom, and wherein the second fixation point comprises an opening through which the conduit passes; reorienting the grip arrangement relative to the base structure at the first fixation point to cause a tip of the conduit to pivot about the second fixation point.

Further embodiments are described in the dependent claims.

Systems and methods according to the present invention advantageously allow the surgeon to reposition a light or fluid conduit within the surgical field and fix it in the desired position throughout the procedure. Moreover, by providing the first fixation point on a surface remote from the immediate surgical field, the number of bulky instruments arranged around the circumference of the eye is reduced. Finally, the mechanically simple arrangement of the present invention facilitates cleaning of the system components and economically allows for replacement of the component parts after one use or more uses.

SHORT DESCRIPTION OF THE DRAWINGS

Exemplary embodiments of the invention will now be described with reference to the attached drawings, in which:

FIG. 1 shows a conduit steering system in accordance with an embodiment of the present invention;

FIGS. 2A-B show the system of FIG. 1 in situ in an ophthalmic surgical setting; and FIGS. 3A-F show six possible orientations for the system of FIGS. 1 and 2 in use.

DESCRIPTION OF EMBODIMENTS

FIG. 1 shows a system for positioning a conduit within an ophthalmic surgical field in accordance with one exemplary embodiment of the present invention. As shown in FIG. 1, the system 10 comprises a conduit 12 for delivering light or fluid to the eye 1. A first fixation point 14 comprises a base structure 16 arranged to be secured in a fixed location, and a grip arrangement or grip component 18 configured to hold the conduit 12. The grip arrangement 18 is mounted on the base structure 16 by way of a ball joint structure 20, 22. The ball joint structure is arranged to allow pivoting and rotational movement of the grip arrangement 18 with respect to the base structure 16 (e.g. whilst preventing translation movement of the grip arrangement 18 and the base structure 16 with respect to each other). A second fixation point 15 is positioned remote from the first fixation point 14 at a predefined distance therefrom.

The first fixation point 14 can be clipped onto the conduit 12 approximately 50-200 mm from the proximal end 12a of the conduit 12. This allows the first fixation point 14 to be positioned away from the eye, freeing up valuable space around the surface of the eye.

Advantageously, the second fixation point 15 is located at the entry to the surgical site, i.e. at or near the surface of the eye 1. The second fixation point 15 can comprise any structure that provides access to the interior of the eye 1. For example, the second fixation point 15 can comprise a cannula 24. The cannula 24 can comprise a simple tube, inserted into the eye 1 with an insertion device (not shown), through which the conduit 12 can be passed to reach the interior of the eye 1. Alternatively, the cannula 24 can comprise a sharp tip to facilitate insertion into the eye 1. The skilled person will also understand that the second fixation point 15 can comprise a trocar arrangement, comprising a port (e.g. a cannula), which incorporates a seal or fixation feature for engaging the conduit 12. One exemplary embodiment of this nature will be discussed below with reference to FIG. 2B.

As shown in FIG. 1, the conduit 12 can be configured as a light conduit comprising at least one optical fibre. In this embodiment, the distal end of the conduit 12 is coupled to a light source L. The optical fibre delivers light from the light source to the eye 1. Alternatively (or additionally), the conduit 12 can be configured as a fluid conduit comprising at least one internal lumen for delivering fluid to or from the surgical site (e.g. an infusion line or an aspiration line). The fluid conduit can be coupled to a source of irrigation fluid (e.g. an infusion bottle) and configured to deliver irrigation fluid to the eye 1. Alternatively, the fluid conduit can be coupled to a vacuum source and configured to evacuate surgical fluid and/or surgical debris from the surgical site. Multiple lumens can be provided in a single conduit 12.

As shown in FIG. 1, the system 10 can further comprise a sheath 26 which surrounds the conduit 12 at least partially along its length. In some embodiments, the sheath 26 can surround the conduit 12 in the region of the first fixation point 14. This can provide additional protection to the conduit 12 (e.g. an optical fibre) in the region of the grip arrangement 18.

In addition to providing protection for the conduit 12, the sheath 26 can be used to increase the stiffness of the conduit 12 as required. For example, the combination of the sheath 26 and the conduit 12 can have a greater stiffness than the exposed portion of the conduit 12. This can be achieved by forming the sheath from a material that has a greater flexural modulus than the conduit 12. Alternatively, the sheath 12 may be formed of a material having a similar flexural modulus to the conduit, whereby the increase in stiffness is provided by the increased total dimeter of the conduit 12 and the sheath 26. By leaving the proximal tip 12a of the conduit 12 exposed, the stiffness of the conduit 12 can be varied along its length, with the part surrounded by the sheath 26 being stiffer than the exposed portion at the tip 12a. By providing a more flexible portion of the conduit at the tip 12a, the manoeuvrability of the conduit 12 within the surgical field can be improved. The skilled person will appreciate that the sheath 26 can also be configured to increase the frictional engagement between the grip arrangement 18 and the conduit 12, thereby increasing the stiffness of the coupling between the conduit 12 and the grip arrangement 18. For example, the sheath 26 may comprise surface features along part of its length to facilitate engagement with the grip arrangement 18.

In one exemplary embodiment, the conduit 12 extends from proximal end of the sheath 26 by approximately 5-50 mm, (e.g. approximately 30 mm). This extended length has been found to provide sufficient manoeuvrability of the conduit tip 12a within the eye, whilst protecting the portion of the conduit 12 positioned away from the surgical field.

Referring still to FIG. 1, the ball joint structure 20, 22 can comprise a ball element 20 and a receiving element 22. The receiving element 22 is configured to at least partially confine the ball element 20 therein to prevent translational movement of the ball element 20 with respect to the receiving element 22.

The skilled person will appreciate that such a ball joint structure 20, 22 can be configured in different ways. For example, as shown in FIG. 1, in one configuration, the ball element 20 can be mounted on the base structure 16 and the grip arrangement 18 can comprise the receiving element 22. The ball element 20 is received in the receiving element 22 and secured therein such that relative rotational movement between the ball 20 and the receiving element 22 is permitted to at least some extent in all directions, whilst preventing relative translation between the ball and the receiving element 22 in any direction. As an alternative to the configuration shown in FIG. 1, the base structure 16 can comprise the receiving element 22 and the ball element 20 can be mounted on the grip arrangement 18.

In either case, the receiving element 22 can comprise a partial spherical shell that completely encases the upper part of the ball element 20. Alternatively, as shown in FIG. 2, the receiving element 22 can comprise two or more opposing claws that engage the ball element 20. The claws can be resiliently flexible such that they can be clipped over the ball element 20. Other configurations will be apparent to the person skilled in the art in light of the present disclosure.

The coupling between the ball element 20 and receiving element 22 can be configured with a stiffness that holds the grip arrangement 18 relative to the base structure 16 in a stable position but allows repositioning of the grip arrangement 18 relative to the base structure 16 by a user. In other words, the ball joint structure 20, 22 can be configured to support the grip arrangement 18 in a stable position relative to the base structure 16 until a predetermined repositioning force is applied to move the grip arrangement 18 relative to the base structure 16. The repositioning force can be chosen based on the parameters of the system, e.g. the stiffness and weight of the conduit, the size of the ball joint structure, the proximity to the surgical field, etc. In one example, a suitable repositioning force can be at least 1N (e.g. at least 1.8N). This repositioning force allows the user to easily reposition the grip 18 relative to the base 16, but is high enough to prevent accidental movement of the conduit 12 during a surgical procedure. The skilled person will appreciate that this value can be adjusted depending of the implementation.

Similarly, the stiffness of the coupling between the conduit 12 and the grip arrangement 18 should be chosen such that the grip arrangement 18 engages the conduit 12 with a stiffness that holds the conduit 12 in a stable position relative to the grip position but allows repositioning of conduit 12 relative to the grip arrangement relative to the base structure 16 by a user. In other words, the grip arrangement 18 is configured to support the conduit 12 in a stable position relative to the grip position until a predetermined repositioning force is applied to move the conduit 12 relative to the grip arrangement 18. The repositioning force for moving the conduit 12 axially with respect to the grip 18 can also be chosen based on the parameters of the system, e.g. the stiffness and weight of the conduit, the proximity to the surgical field, etc. In one example, a suitable repositioning force can be at least 0.4N (e.g. at least 0.8N). This repositioning force allows the user to easily reposition the conduit 12 relative to the grip 18 but is stiff enough to prevent accidental movement of the conduit 12 during a surgical procedure. The skilled person will appreciate that this value can be adjusted depending of the implementation. In at least some embodiments, the grip 18 can be configured to exert a force on the conduit 12 that deforms the sheath 26. The deformation of the sheath 26 in turn grips the conduit 12 and prevents axial movement of the conduit 12 relative to the grip 18. The frictional engagement between the sheath 26 and the conduit 12 can be modified by the use of high friction materials for the sheath 26. For example, the sheath 26 can comprise at least a region of silicone or rubber tubing to increase the frictional engagement between the conduit 12 and the grip 18. In addition or as an alternative, the sheath 26 can comprise surface features (e.g. internal or external ribs) to increase the frictional engagement between (i) the conduit 12 and the sheath 26; and/or (ii) the sheath 26 and the grip 18.

The skilled person will recognise that the stiffness of the ball joint structure 20, 22 and the force exerted by the grip arrangement 18 on the conduit 12 can also be chosen depending on the application. In any event, the frictional engagement between the grip arrangement 18 and the conduit 12 or sheath 26 should be sufficient that the grip arrangement 18 can support the conduit's 12 own weight without slipping relative to the grip arrangement 18 and prevent inadvertent repositioning of the conduit 12 relative to the grip arrangement 18 due to incidental contact with the surgeon during the course of a procedure. Instead, the frictional engagement between the grip arrangement 18 and the sheath 26 or conduit 12 should be sufficient such that it prevents movement of the conduit 12 relative to the grip arrangement 18 unless the grip arrangement 18 is actively repositioned by a healthcare professional. This frictional engagement advantageously allows the surgeon to secure the conduit 12 in place for the duration of a procedure (or until deliberately repositioned), leaving both hands free to continue other manual tasks during the procedure. Optionally, to facilitate this capability, the grip arrangement may comprise a release mechanism (such as a pinchable section) that releases the grip's 18 engagement with the conduit 12 and allows repositioning of the conduit 12 relative to the grip arrangement 18.

Referring now to FIG. 2, the base structure 16 of the first fixation point 14 can comprise at least one securing element 28 adapted to secure the base structure 16 to a surface 30. The securing element 28 can comprise an area of adhesive 28 or a clip (not shown) configured to attach the base structure 16 to a surgical drape 30 or other stable surface during the surgical procedure. The skilled person will appreciate that other securing solutions are possible.

As shown in FIG. 2A, the second fixation point 15 is located at or near the surface of the eye 1. In some embodiments, the second fixation point 15 is located at an incision in the surface of the eye 1 (e.g. the sclera). In the embodiment shown in FIG. 2, the second fixation point 15 is provided by a hollow tube or cannula 24 provided at an incision site at the surface of the eye 1. The conduit 12 extends through the second fixation point 15 such that its tip 12a is disposed within the eye 1. Although the embodiment shown in FIG. 2 employs a cannula 24 to provide the second fixation point 15, in some embodiments of the present invention, the cannula 24 can be omitted and the second fixation point 15 can simply be provided by the tissue surrounding the incision in the eye 1.

Referring now to FIG. 2B, the second fixation point 15 can comprise at least one fixation feature 32 adapted to engage the conduit 12 and restrict axial movement of the conduit 12 relative to the second fixation point 15. In other words, the fixation features can prevent the conduit sliding through the opening in the surgical site. The fixation feature 32 can comprise a slit valve, a resilient circumferential ridge, or other interior surface feature that engages the outer surface of the conduit 12. The purpose of the fixation feature 32 is to restrict axial movement of the conduit 12 within the cannula 24 (i.e. sliding of the conduit 12 within the hollow body of the cannula 24) unless a predetermined force threshold is exceeded. For example, the engagement between the cannula 24 and the conduit 12 should be sufficient that the conduit 12 is held in position by its engagement with the cannula 24 unless deliberately repositioned by a healthcare professional.

To facilitate the engagement between the cannula 24 and the conduit 12, the cannula 24 may also comprise an engagement feature 34 configured to engage the corresponding fixation feature 32 on the cannula 24. As shown in FIG. 2B, the engagement feature 34 can take the form of a circumferential ridge provided around the outer surface of the conduit 12. In some embodiments, this feature can be employed in addition to or instead of the fixation feature 32. In yet further embodiments, the cannula 24 and the conduit 12 may be permanently engaged with each other (e.g. fixedly attached).

Use of the system will now be described with reference to FIGS. 3A-F. As shown in FIGS. 3A-F, fixation of the flexible conduit 12 at two pre-determined and spaced fixation points provides two pivot points about which the conduit 12 can move. As the surgeon moves the grip arrangement 18 relative to the base structure 16 at the first fixation point 14, the conduit 12 flexes and pivots about the second fixation point 15. Therefore, generally speaking, a method for positioning a conduit 12 within a surgical field comprises the steps of: (i) securing a conduit 12 at a first fixation point 14 (the first fixation point 14 comprising a base structure 16 configured to be secured to a surface, and a grip arrangement 18 configured to hold the conduit 12 and mounted on the base structure 16 by way of a ball joint structure 20, 22 arranged to allow pivoting and rotational movement of the grip arrangement with respect to the base structure 16); (ii) securing the conduit 12 at a second fixation point 15 (the second fixation point 15 comprising an opening through which the conduit 12 passes and being located at an entry point of the surgical field and remote from the first fixation point 14); and (iii) reorienting the grip arrangement 18 relative to the base structure 16 at the first fixation point 14 causes a tip 12a of the conduit 12 to pivot about the second fixation point 15.

In preparation for or during a procedure, a healthcare provider can create an incision in the eye to provide access for the conduit 12 to the surgical field. As mentioned above, the incision can form the second fixation point 15 or the second fixation point 15 can be provided by the cannula 24. In this case, the method further comprises passing the conduit 12 through the cannula 24. The skilled person will be aware of a number of suitable devices for inserting the cannula into the eye 1. For example, a dedicated entry tool can be used, which both forms the incision in the eye and places the cannula 24. The entry tool is then removed leaving the cannula 24 secured in place, extending through the surface of the eye 1.

Figure 3A:
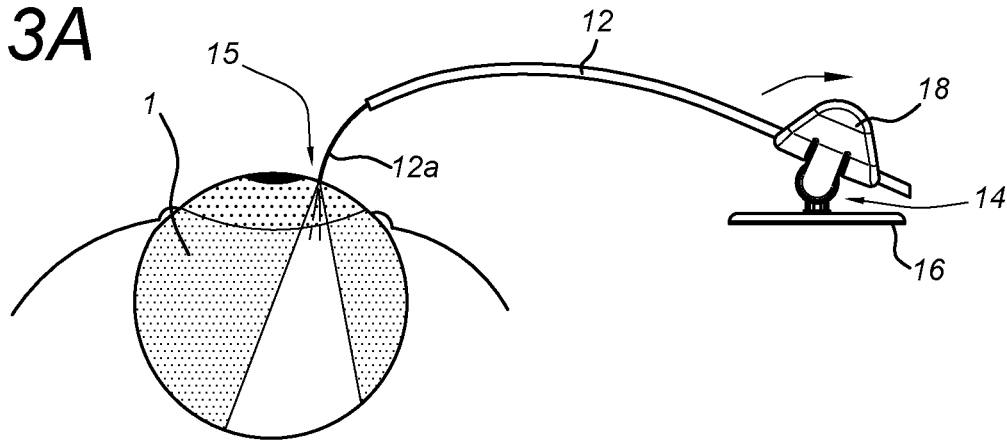
Figure 3B:
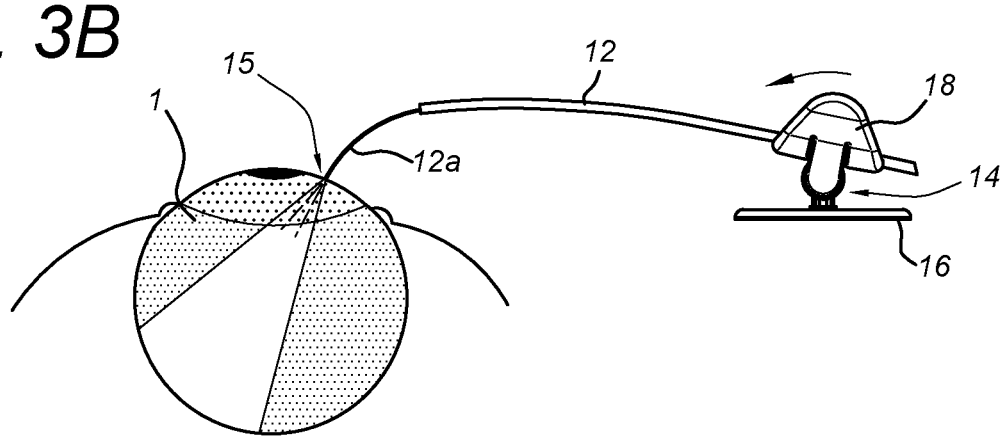

As shown in FIG. 3A, if the grip arrangement 18 is tilted away from the surgical site, the proximal tip 12a of the conduit 12 pivots about the second fixation point 15 to illuminate the back of the eye 1. As illustrated in FIG. 3B, if the grip arrangement 18 is tilted towards the eye, the tip 12a pivots about the second fixation point 15 to illuminate the lower left portion of the eye 1 (as shown in FIG. 3B).

Figure 3C:
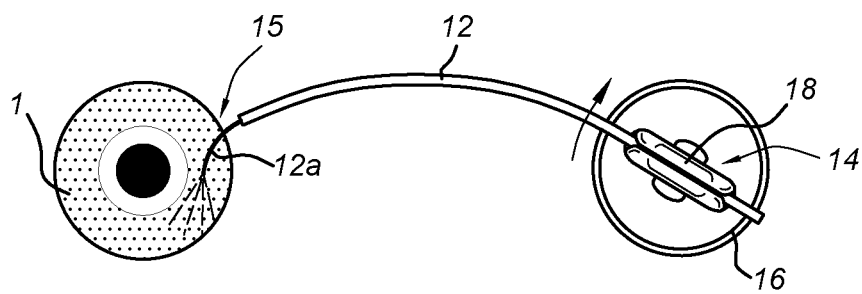
Figure 3D:
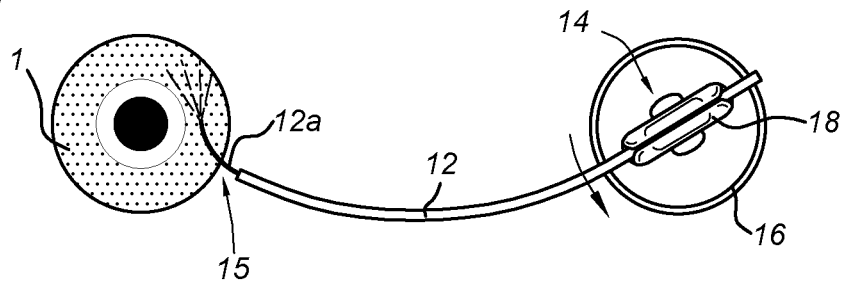

FIGS. 3C and 3D illustrate how the grip arrangement 18 can be manoeuvred to illuminate the left- and right-hand sides of the eye 1 (from the perspective shown in FIGS. 3C and 3D) by twisting the grip arrangement 18 right and left relative to the base structure 16.

Figure 3E:
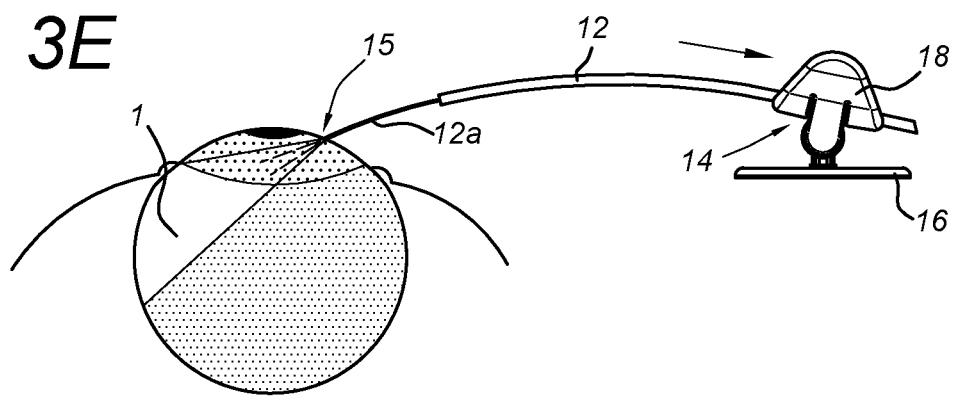
Figure 3F:
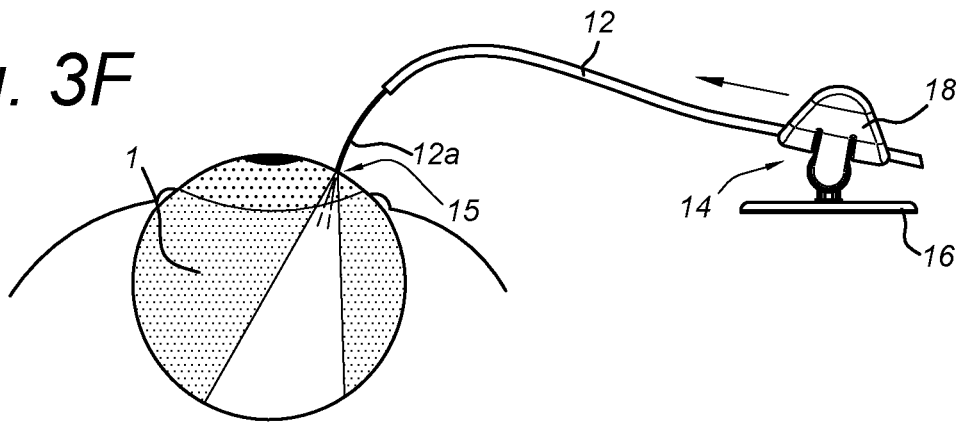

Finally, FIGS. 3E and 3F show how sliding the conduit 12 axially relative to the grip arrangement 18 can be used to steer the tip of the conduit 12 within the eye. As shown in FIGS. 3E to 3F, varying the length of the conduit 12 between the two stable fixation points 14, 15 can alter the field of illumination within the eye 1. As shown in FIG. 3E, the shorter the length of the conduit 12 between the first and second fixation points 14, 15, the straighter the path of the conduit 12 is, resulting in a field of illumination that extends generally along the axis of the conduit 12 between the first and second fixation points 14, 15. In the configuration shown in FIG. 3E, where the first fixation point 14 extends towards the eye from the right-hand side, this results in a field of illumination on the left side of the eye 1. Conversely, if the conduit 12 is slid axially relative to the grip arrangement 18 such that the length of the conduit 12 between the first and second fixation points 14, 15 significantly exceeds this distance between the first and second fixation points 14, 15, the conduit 12 flexes or buckles about the second fixation point 15 and illuminates the back side of the eye 1.

Thus, by repositioning the grip arrangement 18 relative to the first fixation point 14, the proximal tip 12a of the conduit 12 pivots about the second fixation point 15, and an optical fibre or fluid conduit can be steered to illuminate or irrigate and/or aspirate a predetermined region of the surgical field.

The present invention has been described herein with reference to a number of non-limiting exemplary embodiments as shown in the drawings. Once apprised of the present disclosure, the skilled person will appreciate that modification may be made to the embodiments described without departing from the scope of the present invention, which is defined by the appended claims.

The invention claimed is:

1. A system for positioning a conduit within an ophthalmic surgical site, the system comprising:
    a conduit;
    a first fixation point comprising:
    a base structure arranged to be secured in a fixed location, and
    a grip arrangement configured to hold the conduit, the grip arrangement being mounted on the base structure by way of a ball joint structure, the ball joint structure being arranged to allow pivoting and rotational movement of the grip arrangement with respect to the base structure, and
    a second fixation point positioned remote from the first fixation point at a predefined distance therefrom.

2. The system according to claim 1, wherein the second fixation point comprises a cannula.

3. The system according to claim 1, wherein the conduit is configured as an optical conduit and comprises at least one optical fibre.

4. The system according to claim 1, wherein the conduit comprises at least one internal lumen configured to deliver fluid to or from the surgical site.

5. The system according to claim 1, further comprising a sheath surrounding the conduit at least partially along its length.

6. The system according to claim 5, wherein the sheath surrounds the conduit in a region of the first fixation point.

7. The system according to claim 5, wherein the combination of the sheath and the conduit has a greater stiffness than an exposed portion of the conduit.

8. The system according to claim 5, wherein the conduit extends from a proximal end of the sheath.

9. The system according to claim 1, wherein the ball joint structure comprises a ball element and a receiving element, the receiving element configured to at least partially confine the ball element therein to prevent translational movement of the ball element with respect to the receiving element.

10. The system according to claim 9, wherein the ball element is mounted on the base structure and the grip arrangement comprises the receiving element.

11. The system according to claim 9, wherein the base structure comprises a receiving element and wherein the ball element is mounted on the grip arrangement.

12. The system according to claim 1, wherein the ball joint structure is configured to support the grip arrangement in a stable position relative to the base structure until a predetermined repositioning force is applied to move the grip arrangement relative to the base structure.

13. The system according to claim 1, wherein the grip arrangement is configured to support the conduit in a stable position relative to the grip arrangement until a predetermined repositioning force is applied to move the conduit relative to the grip arrangement.

14. The system according to claim 1, wherein the base structure comprises at least one securing element adapted to secure the base structure to a surface.

15. The system according to claim 1, wherein the second fixation point comprises at least one fixation feature adapted to engage the conduit and restrict axial movement of the conduit relative to the second fixation point.

16. The system according to claim 15, wherein the conduit comprises an engagement feature adapted to engage the fixation feature on a cannula.

17. A method for positioning a conduit within a surgical site, the method comprising:
    securing a conduit at a first fixation point, the first fixation point comprising a base structure configured to be secured to a surface, and a grip arrangement configured to hold the conduit, the grip arrangement being mounted on the base structure by way of a ball joint structure arranged to allow pivoting and rotational movement of the grip arrangement with respect to the base structure;
    securing the conduit at a second fixation point at an entry point of the surgical site, wherein the second fixation point is positioned remote from the first fixation point and a predetermined distance therefrom, and wherein the second fixation point comprises an opening through which the conduit passes;
    reorienting the grip arrangement relative to the base structure at the first fixation point to cause a tip of the conduit to pivot about the second fixation point.

18. The method according to claim 17, wherein the second fixation point comprises a cannula and the method comprises the step of passing the conduit through the cannula.

19. The method according to claim 17, further comprising the step of sliding the conduit axially relative to the grip arrangement.

20. The method according to claim 17, wherein the conduit comprises an optical fibre and wherein the step of reorienting the grip arrangement relative to the base structure comprises steering the optical fibre to provide illumination to a pre-determined region of the surgical site.

21. The method according to claim 17, wherein the conduit comprises a fluid conduit and wherein the step of reorienting the grip arrangement relative to the base structure comprises steering the fluid conduit to provide irrigation or aspiration to a predetermined region of the surgical field.

* * * * *